United States Patent
Turner et al.

(10) Patent No.: US 9,795,670 B2
(45) Date of Patent: Oct. 24, 2017

(54) ANTIVENOM

(75) Inventors: Josef Turner, Haifa (IL); Salim K. Amiyreh, Amman (JO)

(73) Assignee: ASELLUS LIMITED, London (GB)

( * ) Notice: Subject to any disclaimer, the term of this patent is extended or adjusted under 35 U.S.C. 154(b) by 697 days.

(21) Appl. No.: 13/883,111

(22) PCT Filed: Nov. 2, 2011

(86) PCT No.: PCT/IL2011/050001
§ 371 (c)(1),
(2), (4) Date: Jul. 18, 2013

(87) PCT Pub. No.: WO2012/059928
PCT Pub. Date: May 10, 2012

(65) Prior Publication Data
US 2013/0302254 A1 Nov. 14, 2013

Related U.S. Application Data

(60) Provisional application No. 61/456,117, filed on Nov. 2, 2010.

(51) Int. Cl.
| | | |
|---|---|---|
| *A61K 39/00* | (2006.01) | |
| *A61K 39/395* | (2006.01) | |
| *C07K 16/06* | (2006.01) | |
| *C07K 16/18* | (2006.01) | |
| *A61K 31/57* | (2006.01) | |
| *A61K 45/06* | (2006.01) | |

(52) U.S. Cl.
CPC ............ *A61K 39/395* (2013.01); *A61K 31/57* (2013.01); *A61K 45/06* (2013.01); *C07K 16/06* (2013.01); *C07K 16/065* (2013.01); *C07K 16/18* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 5,340,923 A | 8/1994 | Carroll | |
| 5,904,922 A * | 5/1999 | Carroll | C07K 16/02 424/130.1 |
| 2003/0113892 A1 | 6/2003 | Hammock et al. | |

FOREIGN PATENT DOCUMENTS

WO 91/06306 A1 5/1991

OTHER PUBLICATIONS

Devaux et al (Journal of Immunological Methods, 2002, 271:37-46).*
Gomes et al (Indian J of Experimental Biology, 2010, 48:93-103).*
Wang et al (Journal of Neuro-Oncology, 2005, 73:1-7).*
Murthy et al. Investigations on the role of insulin and scorpion antivenom in scorpion envenoming syndrome. J. Venom. Anim. Toxins Incl. Trap. Dis. 2003, vol. 9, No. 2.
Petricevich et al. Macrophage activation, phagocytosis and intracellular calcium oscillations induced by scorpion toxins from Tilyus serrulatus. Clin. Exp. Immunol. Dec. 2008 (Dec. 208), vol. 154, No. 3, pp. 415423; abstract.
Zhang et al. Potassium channels and proliferation and migration of breast cancer cells. Acta Physiologica Sinica. Feb. 25, 2009 (Feb. 25, 2009), vol. 61, No. 1, pp. 15-20; abstract.
Ulus et al. Restoration of blood pressure by choline treatment in rats made hypotensive by haemorrhage. Br. J. Pharmacol. Sep. 1995 (Sep. 1995), vol. 116, No. 2, pp. 1911-1917; abstract; p. 1971, para 1.
Boyer et al., (2009) Antivenom for Critically Ill Children with Neurotoxicity from Scorpion Stings. N. Engl J Med 360: 2090-2098.
Devaux et al., (1997) Monoclonal antibodies neutralizing the toxin II from Androctonus australis hector scorpion venom: usefulness of a synthetic, non-toxic analog. FEBS Lett 412(3): 456-460.
Devaux et al., (2002) A strategy for inducing an immune response against Androctonus australis scorpion venom toxin I in mice. Production of high-affinity monoclonal antibodies and their use in a sensitive two-site immunometric assay. J Immunol Methods 271(1-2): 37-46.
Ismail et al., (1998) Pharmacokinetics of 1251-labelled IgG, F(ab')2 and Fab fractions of scorpion and snake antivenins: merits and potential for therapeutic use. Toxicon 36(11): 1523-1528.
Mousli et al., (1999) A recombinant single-chain antibody fragment that neutralizes toxin II from the venom of the scorpion Androctonus australis hector. FEBS Lett 442(2-3): 183-188.
Polyvalent Scorpion Antivenom; retrieved from http://www.antivenom-center.com/navpc-products/polyvalent-scorpion-antivenom/ on Jan. 16, 2017; 2 pages.

* cited by examiner

*Primary Examiner* — Laura B Goddard

(57) ABSTRACT

The use of scorpion antivenom for the manufacture of a medicament for treatment of hypertension and/or cancer in a subject is disclosed as well as the treatment of the subject.

20 Claims, 2 Drawing Sheets

ANTIVENOM

CROSS-REFERENCE TO RELATED APPLICATIONS

This patent application is a §371 National Phase filing of co-pending PCT Patent Application No. PCT/IL2012/050001, filed Nov. 2, 2011, which is based upon and claims the benefit of the filing date of U.S. Provisional Patent Application Ser. No. 61/456,117, filed Nov. 2, 2010, each of which is incorporated herein by reference in its entirety.

FIELD OF THE INVENTION

The present invention relates to uses of scorpion antivenoms.

BACKGROUND OF THE INVENTION

A great deal of cancer research centers on the problem of how to selectively kill cancer cells.

Although there was a great improvement in treating cancerous malignancies in the last decade, many patients with metastatic cancer disease fall chemotherapy and other oncology treatments, becoming resistance to the oncology drugs and will die from cancer. Additional drugs should be developed and used for the treatment of those patients.

Many chemotherapy drugs used in oncology affect cancer cells in different ways and in different cell cycle phases. Biological targeting dugs can affect cancer cells by their effect on epidermal growth factor receptors (EGFRs) as the Tyrosine kinase inhibitors. Other biological targeting drugs affect the vascular endothelial growth factor receptors (VEGFRs) and act as anti angiogenetics.

All drugs used in oncology have many side effects, some of them are life threatening. Grade 3 and 4 toxicities are relatively common and can cause death in cancer patients. Often patients have to stop chemotherapy and other drug treatments because of the severe side effects. This may lead to the progression of the disease. If patients have decreased liver and kidney function tests they cannot be given most of the recent oncology drugs. Most chemotherapy drugs affect the bone marrow leading to neutropenia and/or thrombocytopenia and anemia which makes the continuation of treatment an impossible mission.

Chlorotoxin is a 36-amino acid peptide found in the venom of the deathstalker scorpion (*Leiurus quinquestriatus*) which blocks small-conductance chloride channels, Chlorotoxin binds preferentially to glioma cells, which has the potential to fundamentally improve intraoperative detection and resection of malignancies [Mandana Veiseh et al., *Cancer Res.*, 2007; 67:6882-6888].

Serotherapy is considered to be the only specific treatment against envomenation by scorpions, i.e., patients stung by scorpions are treated with antivenoms, antibodies such as Immunoglobulin or parts thereof, directed towards neutralization of the active pharmacological sites of the venom [M. Ismail, Toxicon, 1994; 32(9): 1019-1026]. In particular, reduction of adverse reaction has been achieved by deleting the Fc part of the antivenom Immunoglobulin, leaving the F(ab')$_2$ part of the immunoglobulin for treatment. Free F(ab')$_2$ $_{may}$ not complex to venom, for example due to the venom already-binding to cellular receptors before the treatment is initiated. However, the antivenom may remove toxins fixed on their receptors [Ghalim N. et al., Am. J. Trop. Med. Hyg., 2000; 62(2): 277-283].

The immunoglobulin fractions IgG, F(ab')$_2$ and Fab of scorpion and snake Antivenoms do not bind to the receptors. It is well known that antibodies do not have the pharmacological activity of their antigens. The antivenom antibodies and their fractions possess pharmacokinetic characteristics that are significantly different from their respective venoms. For example, the venoms and their toxins) are several fold faster in their distribution into the tissues than any of the immunoglobulin fractions [M. Ismail and M. A. Abd-el-salam, Toxicon 1998; 38(11): 1523-1528]. Therefore, any indication of a toxin being effective against some type of cancer is not an indication of the effectiveness of the toxin antibody or fraction thereof.

A few types of cancer cells are especially vulnerable to selective attack because they depend on specific hormones or because their surfaces have unusual chemical features that can be recognized by antibodies. However, it is estimated that even in the absence of antigen stimulation a human makes at least $10^{15}$ different antibody molecules. In general, therefore, progress with the vexing problem of anticancer selectivity has been slow—a matter of trial and error and guesswork as much as rational calculation. [Alberts, Bruce et al., Molecular Biology of the Cell, $3^{rd}$ Ed., p. 1267, Garland Publishing, Inc., New York & London].

Therefore, there is no known indication of the effectiveness of antivenoms against cancer. In particular, there is no indication of the effectiveness of scorpion antivenoms against cancer.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

SUMMARY OF THE INVENTION

Figure 1:
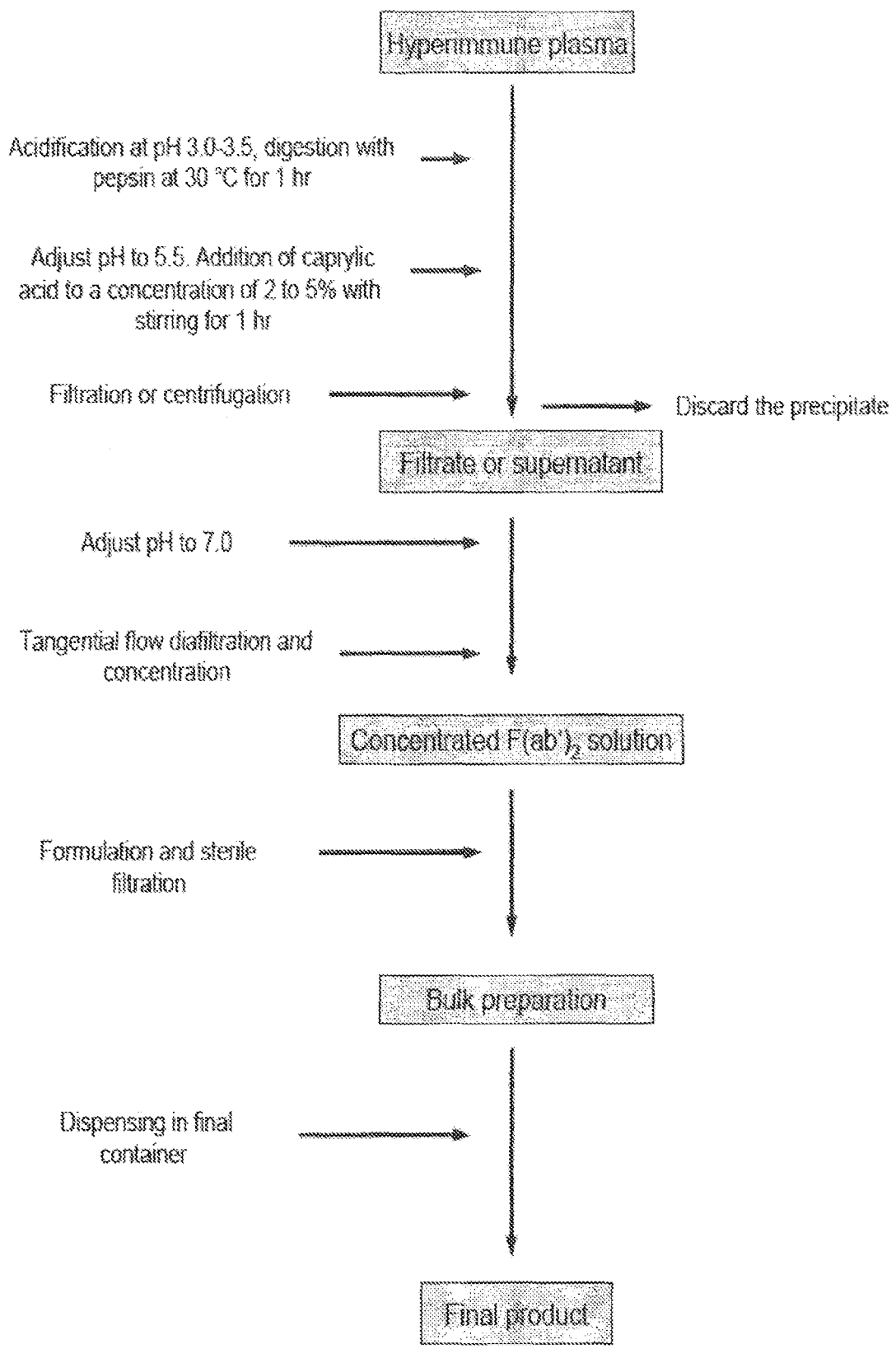
FIG. 1 shows an example of a fractionation process in which F(ab')$_2$ antivenom fragments are prepared by pepsin digestion and caprylic acid precipitation.

According to one aspect, use of scorpion antivenom for the manufacture of a medicament for treatment of hypertension and/or cancer in a subject is provided.

In preferred embodiments, the medicament comprises Immunoglobulins and/or fragments thereof purified from the antivenom.

More preferably, the fragments comprise one or more Fab and/or F(ab')2.

The immunoglobulins may be one or more of: IgA, IgD, IgE, IgG and IgM.

The antivenom may be from at least one mammal, for example: horse, goat, pig, sheep, rabbit and/or camel.

In some embodiments, the medicament comprises macrophages and/or neutrophils having receptors for antigens in scorpion antivenom.

The antivenom may be produced from envomenation of at least one animal with the venom or toxins thereof from at least one scorpion.

The scorpions are for example one or more of the group of species comprising:

*androctonus bicolor, androctonus crassicauda, apistobuthus pterygocercus, buthacus buettikeri, buthacus yotvatensis nigroaculeatus, butheolus anthracinus, butheolus villosus hendrixson, compsobuthus arabicus, compsobuthus fuscalus, compsobuthus longipalpis, compsobuthus pallidu, compsobuthus setosus, hottentotta jayakari jayakari, leiurus jordanensis, leiurus quinquestriatus, orthochirus innesi, parabuthus leiosoma leiosoma, vachoniolus globimanus, hemiscorpius arabicus, nebo hierichonticus, pandinus* (*pandinurus*) *arabicus, pandinus* (*pandinurus*) *exitialis, scorpio maurus arabicus, scorpio maurus fuscus, scorpio maurus kruglovi*, and *scorpio maurus* sspp., *buthus arenicola, buthus mimax, buthus occitanus, leiurus quinquestriatus hebreus* and *androctonus amoreuxi*.

The manufacture may comprise: collecting at least one scorpion venom;

preparing an immunizing dose of the venom;

injecting the immunizing dose to an animal;

collecting plasma serum separated from blood from the animal, and fractionating plasma immunoglobulins.

The immunizing dose may comprise a venom mixture.

Preferably, the injection is subcutaneous or intramuscular.

In some embodiments, the treatment comprises:

providing the medicament in one of the following to the subject; intramuscular injection of a solution of the antivenom, orally introducing an enteric coated antivenom medicament, a spray comprising the antivenom or a sustained release medicament, and per rectum introducing a suppository.

In preferred embodiments, the treatment is by injection, it preferably further comprises injecting an analgesic.

Preferably, an allergy examination of the subject is conducted before providing the medicament, the allergy examination comprising applying the medicament to the subject's skin and observing the skin for inflammation, swelling or other allergic response.

According to another aspect of the invention, treatment of hypertension and/or cancer in a subject is provided, wherein the treatment comprises administering a medicament comprising a scorpion antivenom to the subject, the medicament comprises Immunoglobulins and/or fragments thereof purified from the antivenom.

The treatment of any one of the claims may further comprise:

providing the medicament in one of the following to the subject: intramuscular injection of a solution of the antivenom, orally introducing an enteric coated antivenom medicament, a spray comprising the antivenom or a sustained release medicament, and per rectum introducing a suppository.

The treatment may further comprise allergy examination of the subject before providing the medicament, the allergy examination comprising applying the medicament to the subject's skin and observing the skin for inflammation, swelling or other allergic response.

In some embodiments, the medicament comprising a scorpion antivenom is administered at least twice.

Preferably, the administration is at least 7 days apart.

The treatment may further comprise measuring progression in treatment, the measuring comprising one or more of the following parameters on the subject:

measuring blood pressure and cardiac pulse of the subject before and 1 hour after SVA treatment; physical examination 1 week after first SVA: evaluating patient performance status and tumor size, CBC, CEA, liver function test and kidney function test 10 and 24 days after first treatment, whereby continuation of treatment is determined.

The treatment may further comprise measuring progression in treatment, the measuring comprising one or more of the following parameters on the subject; CEA and X-ray, at least 7 days administering the medicament.

According to yet another aspect of the invention, a hybridoma configured to produce a scorpion antivenom immunoglobulin is provided.

Another aspect is use of a hybridoma configured to produce a scorpion antivenom immunoglobulin for the manufacture of a medicament for treatment of cancer in a subject.

DETAILED DESCRIPTION OF THE INVENTION

It is an object of the present invention to provide a medicament for the treatment of cancer patients to improve their condition.

Hypertension is frequently present in children with scorpion envenomation. The symptom is typically relieved by injection of antivenom preparations specific against scorpion venoms. Therefore, it was thought that antivenom prepared from sera of animals injected with scorpion venoms may also help improve the condition of other patients afflicted with hypertension, even though $F(ab')_2$ fragments of antibodies in the serum, the active ingredient in most commercial preparations against envomenation available today, typically reach peak concern ration in the urinary bladder 5 minutes after an i.v. injection of the antivenom, and 2 hr in the stomach and the intestine [M. Ismail and M. A. Abd-Elsalam, Toxicon, 1996; 34(2): 147], and is not known to have a physiological effect of its own except for binding venom molecules.

Indeed, it became clear to us that the medicament positively affected people suffering from hypertension, such as stabilization of blood pressure, for a limited period of time. However, two of the patients were also suffering from cancer (skin cancer and lung cancer), and surprisingly the condition in relation to the cancer also significantly improved.

Therefore, a decision was made to examine the medicament on patients suffering from various types of cancer, some of which had undergone chemotherapy without improvement of their condition. Over 50 patients have been treated after undergoing an allergy test to ascertain no adverse immune reaction to the antivenom preparation. Overall results were that within about five weeks the cancerous tumors in liver and lungs decreased by at least 50%, and even faster improvement was obtained in patients suffering from breast or prostate cancer. Additional treatments if required continued the apparent healing process up to the disappearance of the tumors.

The following sections describe in short steps examples of preparation of antivenom that may be used in treatment of cancer. Further details about preparation are readily available in the art, such as WHO Guidelines for the Production, Control and Regulation of Snake Antivenom Immunoglobulins, WHO Press, World Health Organization, Switzerland.

Preparation of Venoms

Scorpion antivenoms may be prepared by different methods and employing a variety of techniques. Although crude venoms may be used in the immunization procedure (injection into an animal for development of plasma reflecting an immune response), neurotoxins are present in scorpion venoms in low concentrations and adjoin much larger molecules that are non-toxic or only slightly toxic. Consequently, the use of crude venoms as antigens will cause mainly the production of antibodies against the larger molecules, to the detriment of the action against neurotoxins [M. Ismail, Toxicon 1995; 33(7): 825-858].

Therefore, despite the antivenom presumably acting against agents significantly different in structure from scorpion toxins, in some embodiments the antivenom is prepared from injection of purified toxins to immunized animals.

Nevertheless, it is stressed that for some treatments crude venom may provide improved treatment results.

Preparation of Hyper Immunized Serum

Horses, for example Arabian horses, or other animals such as goats may be immunized, preferably with gradually increasing doses, with the toxic fractions purified from a pool of crude venom by using gel filtration chromatography on Sephadex-G50, which results in a good immunoreactivity of the F(ab')2 as determined by western blot of SDS-PAGE 12.5% gel electrophoresis [M. N. Krifi et al., J. Venom. Anim. Toxins, 1999; 5(2)]. Immunomodulators may also be injected to improve hyper immunization. The venom used for antivenom sera production may be a large pool, for example from more than 10,000 individual milkings. Scorpions of the same species may be collected in many endemic areas to avoid geographical venom variations.

Preparation of Immunogen in Adjuvants

To minimize infection at the immunization sites, all manipulations should be carried out under aseptic conditions. Venom solutions may be prepared in distilled water or phosphate-buffered saline solution (PBS) and filtered through a 0.22-μm membrane. The venom solution is then mixed and/or emulsified with adjuvant such as Freund's complete and incomplete adjuvants, aluminium salts (hydroxide and phosphate), bentonite and liposomes.

Collection and Control of Animal Plasma for Fractionation

Historically, serum separated from the blood of hyper immunized horses was the basis of "antivenin serumtherapy". However, plasma is preferably used as the starling material and undergoes a fractionation process for the separation of purified antivenoms.

Some laboratories have found that using plasma enables higher recovery of antibodies per donation and it is less contaminated with hemoglobin. Separation of plasma from anticoagulated blood is much more rapid than separation of serum from clotted blood.

Purification of F(ab')$_2$ Antivenoms

Studies of the efficacy of the venom antibodies and their enzyme-digestion fractions Fab and F(ab')$_2$ have shown that the fraction F(ab')$_2$ has a higher tissue distribution than Fab [M. Ismail and M. A. Abd-elsalam, Toxicon 1998; 36(11): 1523-1528]. The Fc portion of the antibodies is well-known to elicit undesired immune reactions [M. N. Krifi et al., J. Venom. Anim. Toxins, 1999; 5(2)], [L. V. Boyer et al., the New England Journal of Medicine, 2009; 360:20]; therefore, in many commercial preparations of antivenom, as has now been used in the treatment of cancer patients, the hyper immune plasma is treated to maximize F(ab')$_2$ content, for example by $(NH_4)_2SO_4$ salt fractionation, digestion by pepsin to F(ab')$_2$, and the F(ab')$_2$ then purified, for example by gel filtration [M. Ismail and M. A. Abd-elsalam, Toxicon 1998; 36(11): 1523-1528].

A heating step and salting-out using ammonium sulfate may be used for the purification of F(ab')2 fragments.

The purification may involve performing a pepsin digestion step on a pre-purified fraction that is obtained by treatment of plasma with ammonium sulfate to obtain an IgG-enriched precipitate, whereas albumin is not precipitated.

Pepsin digestion may be accomplished at a pH of 3.0-3.5. A typical protocol is based on incubation at pH 3.3 for 1 hour, at 30-37° C. in a jacketed tank, with a pepsin concentration of 1 g/l. Other procedures can be used which give similar results. For example, the whole serum may be digested before purification of the F(ab')2, which may improve the antigen binding activity of the antivenom [P. P. Kumpalume et al., Food and Byproducts Processing, 2002; 80(2): 88-97].

Downstream processing may be done in one of the two ways:

Downstream Processing Using Ammonium Sulfate

After pepsin digestion, the pH may is adjusted to 4.5-5.0, by adding NaOH or a weak alkaline buffer; then ammonium sulfate is added with stirring to a final concentration usually close to 12% (w:v). The precipitate is eliminated by filtration or centrifugation, and the filtrate, or supernatant, is heat-treated (usually at 56° C.) for 1 hour. After the thermocoagulation, the preparation is cooled down to less than 30° C., e.g. by passing cold water through a jacketed vessel. The resulting fraction is filtered or centrifuged to remove the precipitate. The pH is then adjusted to 7.0"C7.2 with NaOH, and a solution of ammonium sulfate is added with stirring to a final concentration high enough to precipitate the F(ab')2 fragments (usually 23% (w:v) or higher). After an additional filtration step, or following centrifugation, the F(ab')$_2$ precipitate is dissolved, and then desalted (to remove the ammonium sulfate) and further purified and concentrated, preferentially by tangential flow diafiltration and dialysis. Care should be taken to avoid aggregate formation by ensuring gentle mixing and rapid dissolving of the precipitate. Alternatively, the 23% (w:v) step is bypassed and, directly after the heating step, the filtrate obtained is subjected to ultrafiltration. Additional precipitation may also be applied on the starting material at a low ionic strength and acid pH to remove "euglobulins".

The F(ab')$_2$ solution is then formulated by adding NaCl, an antimicrobial agent, and any other excipient needed for formulation, such as protein stabilizers e.g. sodium chloride, sucrose and glycine, and the pH is adjusted, generally to a neutral value. Finally, the preparation is sterilized by filtration through 0.22-μm filters, and dispensed into final containers (vials or ampoules).

Preferably, tangential diafiltration is used for the manufacture of the F(ab')$_2$ fragments. The yield of this fractionation protocol usually ranges between 30% and 40%.

Downstream Processing Using Caprylic Acid

FIG. 1 shows an example of a fractionation process in which F(ab')2 fragments are prepared by pepsin digestion and caprylic acid precipitation, F(ab')2 is not precipitated, therefore reducing the formation of aggregates. Additional processing steps may be use, such as ion-exchange chromatography or ultrafiltration, to eliminate low-molecular-mass contaminants.

Figure 2:
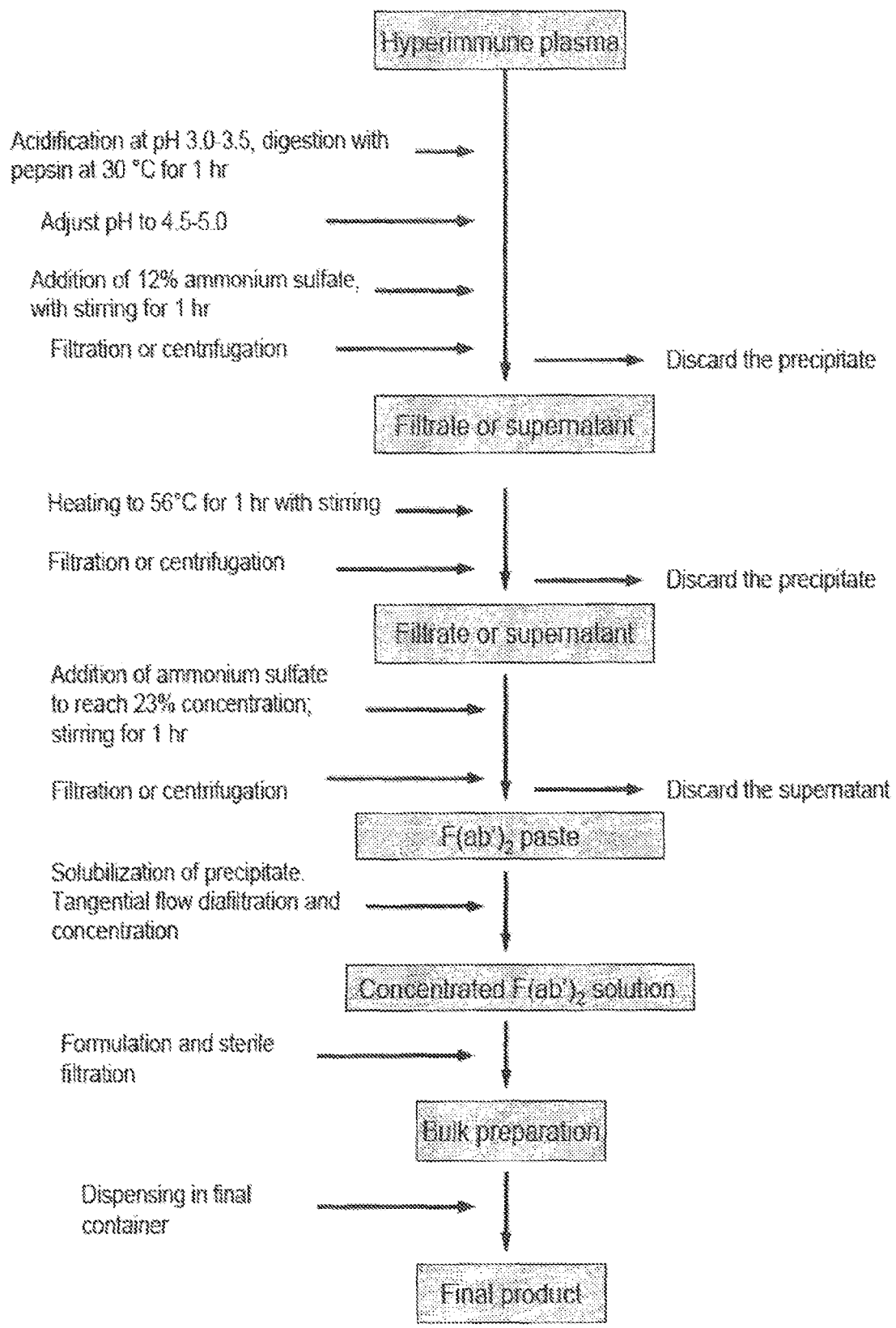
FIG. 2 shows an example of a fractionation process in which F(ab')$_2$ fragments are prepared by pepsin digestion and ammonium sulfate precipitation.

FIG. 2 shows an example of a fractionation process in which F(ab')$_2$ fragments are prepared by pepsin digestion and ammonium sulfate precipitation.

Anion-exchange columns of DEAE or QAE gels or membranes, such as quaternary ammonium cellulose microporous membranes, can be used at neutral pH to adsorb protein contaminants. Alternatively, cation-exchange columns, e.g. carboxymethyl or sulfopropyl gels, may be used for purification of IgG or F(ab')$_2$ fragments. The column is equilibrated at acid pH, e.g. pH 4.5, to bind the antivenom, whereas protein contaminants are eluted in the break-through.

Eventually, if should be possible to produce a hybridoma configured to produce a scorpion antivenom immunoglobulin, which would simplify the process of preparation of a medicament.

Although the active ingredient in commercial preparations for treatment of envomenation is apparently only or predominantly the F(ab')$_2$ fragment of a antivenom-specific antibody, in treatment of patients against cancer it is feasible that other related agents, such as some purified from the crude antivenom, or prepared thereof, may be used in the treatment.

Preliminary Results—Treatment Against Cancer

Polyvalent Scorpion Antivenom, National Antivenom & Vaccine Production Center, Riyadh, KSA, was examined in combination with other supportive generic medicines on healthy people and experienced no side effects.

The polyvalent scorpion antivenom is a refined and highly purified preparation containing the F(ab')$_2$ fractions of the immunoglobulins raised against scorpion venom.

The antivenom is prepared by hyperimmunizing healthy Arabian horses using gradually increasing doses of Saudi scorpion venoms and immunomodulators.

The sera are of high titre and purified by various stages of salt fractionation and pepsin digestion. The resulting (Fab')$_2$ fragments are clarified by gel adsorbents and multistage filtration followed by dilution to the required potency (against scorpion venom). All tests were given after an allergy test for each patient, to examine whether he/she is allergic to the SVA. The test comprised scratching skin of the patient about 2 cm scratch, applying thereon a small amount of antivenom and examining the site of application after about 10 minutes for adverse reaction. Redness and/or swelling around the scratch was monitored, as well as any other suspicious physiological reaction, which would have required to immediately stop treatment of that patient, as well as inject an ampoule of hydrocortisone. However, such reactions were not observed in any of the patients.

Patients were injected one ampoule of the SVA, after local injection of lidocaine HCl; dexamethasone and a nootropic (PIRACETAM) were also injected IM.

Dexamethasone is used to prevent any allergic reaction to the anti venom; the nootropic may help to improve the metabolic environment essential for good neuronal function. It may also help preventing any blood clotting in the body and is also considered to be beneficial for memory.

The four injections were repeated 10 days later. 7-10 days after the second treatment the treatment efficacy was evaluated by X-ray and CEA (Carcinoembryonic Antigen) was also measured whenever possible. In some patients, in particular breast and prostate cancer, there was apparently complete disappearance of cancer—these patients were released and the treatment was complete. In the other patients, treatment was continued for up to two additional treatments 10 days apart, with the tests being repeated between treatments, as before. Patients showing an improvement of only 20-40% (tumor size/CEA count) after the first two treatments were sent home to rest for 2-3 months, and then the injections were recommenced at the rate of 10 injections a day. Generally, the patients with cancer stage 4 showed the slowest recovery rate, and large tumors e.g. in some of the patients having lung cancer required more repeated injections before disappearance.

A small percentage of patients having stage 4 cancers died before the first 40 days of treatment had passed. All the other patients showed no sign of cancer 6-8 months after the treatment had begun.

Sample Cases:

1. A 55 years old female.

Endometrial Cancer with bilateral lung metastases.

Medical history: Open heart surgery.

She received methotrexate with no apparent response.

One month after treatment with SVA chest and abdominal CT showed no disease.

2. A 39 years old male was diagnosed with recurrent squamous cell cancer of Larynx stage III.

He received radiotherapy and cytoxane one cycle, and then refused to continue chemotherapy.

After 3 cycles of SVA a CT scan of the neck showed no abnormalities.

3. A 40 years old male was diagnosed with Cancer of unknown primary with omental and liver metastases seen in the CT.

He received chemotherapy with taxol, oxaliplatin and 5FU. There was no apparent response to the treatment.

After treatment with SVA, the abdominal CT showed no abnormalities.

4. A 53 years old female was diagnosed with ovarian cancer. TAH+BSO were done. Shortly after those omental metastases, ascytis and pleural effusion was observed in a CT scan. She refused chemotherapy.

SVA was given. One month later a CT scan exhibited no abnormalities.

5. A 60 years old female was diagnosed with ovarian cancer of ovary with peritoneal spread and ascites. After failure of one line chemotherapy she was treated with SVA.

The CT after treatment showed no abnormalities and CA125 decreased from high levels to 18.78 (normal level).

Other cases with breast, colon, and prostate and other sites cancers were also treated with SVA; most achieved complete remission.

SVA is effective with both patients who have not received chemotherapy and/or radiations, and those who have received or are receiving these treatments. SVA may be used without all side effects of oncology therapy used today. It may be given also to patients with reduced liver and function tests and to patients with pancytopenia. SVA may open new horizons for the treatment of cancer patients that cannot be treated with the presently commercially available anticancer drugs.

Present Treatment Procedure

The treatment is presently considered to be especially suitable for the group meeting the following criteria:

Inclusion Criteria:

Cancer patients who have all the following criteria;

1. Patients with histological proven cancer disease;
2. Locally advanced or metastatic disease;
3. A measurable disease by physical examination or by imaging or laboratory methods;
4. Performance status 0-2, and
5. Patients who failed previous 1 to 2 lines of therapy for metastatic disease.

Exclusion Criteria:
One of the following:
1. Performance status of 3 and 4;
2. Brain metastases;
3. Patients with poor compliance;
4. Patients treated with immunosuppressive therapy;
5. Patients <18 years old, and
6. Pregnant women.

In particular, the medicament may be useful for treatment against the following cancers: breast, colon, and lung, prostate, malignant lymphoma, at advanced stags or with metastases.

However, in general the medicament is suitable for all patients suffering from cancer.

Before treatment the patients are extensively examined, no more than 3 weeks before treatment, the examination including imaging such as CT, and blood tests. The examination is repeated 5 weeks after treatment begins.

The procedure is carried out each time the patient arrives for a treatment. Treatment is given once weekly for four consecutive weeks.
1. Conducting an allergy test to SVA by a slight scratch of about 2 cm long; waiting for at least 10 minutes. If there is redness and/or swelling around the scratch, or any other suspicious physiological reaction, it is required to immediately stop the treatment of that patient, and act as required by injecting an ampoule of about 4 cc of hydrocortisone. This patient will be taken out of the treatment group. The treatment continues with non-allergic patients,
2. Close to the injection point, the patient is injected with Lidocaine 2%, USP 20 mg/mL, 2 mL (This prevents a sense of burn in the SVA injection area).
3. Injecting to the patient a standard ampoule of SVA to the muscle, for example 4 cc of Polyvalent Scorpion Antivenom, National Antivenom & Vaccine Production Center, Riyadh, KSA, or other scorpion antivenom at equivalent neutralization capacity,
4. The patient is injected—to a muscle—in a different place a standard ampoule of hydrocortisone 1 mg/mL (It serves as anti-allergic protection and prevents overload on the immune system).
5. The patient is injected—to a muscle—a neutrophile ampoule, about 3-4 cc. This injection may improve the blood flow to the brain, relax the nervous system, reduce stress and improve the connections between neurons. It may also prevent blood clots and strokes).
6. The patient is given at least one glass of wafer to drink, and stays at the clinic under observation for at least 15 minutes. The patient may not drive a vehicle for at least 2 hours.

Progression in treatment may be measured by one or more of the following parameters:
Blood pressure and cardiac pulse before and 1 hour alter SVA treatment;
Skin rush/anaphylactic shock after SVA treatment; physical examination 1 week after first SVA: patient performance status and tumor size; CBC, liver function test and kidney function test 10 and 24 days after first treatment;
Response evaluation methods: tumor size (cm) by physical examination; clinical findings: CT scans; bone scan; US; MRI; PET-CT, and tumor makers, classified by type and level: blood count such as WBC, HB and platelets.

Further treatments thereafter may be required according to the response to treatment, i.e., further treatments if symptoms of cancer persist but there is an apparent improvement, or if cancer returns afterwards. The treatments may continue for a period of a year or longer, but perhaps at different doses and frequency than the first treatments, according to the state of the disease and of the patient.

The supportive medicaments, e.g. hydrocortisone and/or nootropic, may also be administered in between SVA treatments. Additional agents that may be administered during the treatment regime are nano-particles comprising silver and/or gold, for example gold nano-particles decorated with argininge-glycine-aspartic acid peptide (RGD), to either or both help kill and to help indicate the cancerous cells. Agents boosting the immune system may also be concomitantly administered. During the treatment regime, as well as afterwards, a diet including food additives and vitamins such as B12 may further help improve the patient's condition and speed up the recovery.

The invention claimed is:

1. Treatment of cancer in a subject, wherein the treatment comprises administering a medicament comprising a scorpion antivenom to the subject.

2. The treatment of claim 1, wherein the medicament comprises immunoglobulins and/or fragments thereof purified from the antivenom.

3. The treatment of claim 2, wherein the fragments comprise one or more Fab and/or F(ab')$_2$.

4. The treatment of claim 2, wherein the immunoglobulins are selected from the group consisting of IgA, IgD, IgE, IgG, and IgM.

5. The treatment of claim 1, wherein the antivenom is from at least one mammal.

6. The treatment of claim 5, wherein the mammal is selected from the group consisting of horse, goat, pig, sheep, rabbit, and camel.

7. The treatment of claim 1, wherein the antivenom is produced from envenomation of at least one animal with the venom or toxins thereof from at least one scorpion.

8. The treatment of claim 7, wherein the scorpions are selected from the group consisting of *androctonus bicolor, androctonus crassicauda, apistobuthus pterygocercus, buthacus buettikeri, buthacus yotvatensis nigroaculeatus, butheolus anthracinus, butheolus villosus hendrixson, compsobuthus arabicus, compsobuthus fuscatus, compsobuthus longipalpis, compsobuthus pallidu, compsobuthus setosus, hottentotta jayakari jayakari, leiurus jordanensis, leiurus quinquestriatus, orthochirus innesi, parabuthus leiosoma leiosoma, vachoniolus globimanus, hemiscorpius arabicus, nebo hierichonticus, pandinus (pandinurus) arabicus, pandinus (pandinurus) exitialis, scorpio maurus arabicus, scorpio maurus fuscus, scorpio maurus kruglovi*, and *scorpio maurus* sspp., *buthus arenicola, buthus mimax, buthus occitanus, leiurus quinquestriatus hebreus*, and *androctonus amoreuxi*.

9. The treatment of claim 1, wherein the medicament comprises a scorpion antivenom manufactured by:
   collecting at least one scorpion venom;
   preparing an immunizing dose of the venom;
   injecting the immunizing dose into an animal;
   collecting plasma serum separated from blood from the animal; and
   fractionating plasma immunoglobulins.

10. The treatment of claim 9, wherein the immunizing dose comprises a venom mixture.

11. The treatment of claim 9, wherein the injection is subcutaneous or intramuscular.

12. The treatment of claim 1, further comprising:
   providing the medicament to the subject in one of the following forms: intramuscular injection of a solution of the antivenom, oral introduction of an enteric coated antivenom medicament, a spray comprising the antivenom or a sustained release medicament, and per rectum introduction of a suppository.

13. The treatment of claim 12, wherein the treatment is by injection, further comprising injection of an analgesic.

14. The treatment of claim 12, further comprising treatment with a cortisone.

15. The treatment of claim 12, further comprising treatment with a nootropic.

16. The treatment of claim 12, further comprising allergy examination of the subject before providing the medicament, the allergy examination comprising applying the medicament to the subject's skin and observing the skin for inflammation, swelling or other allergic response.

17. The treatment of claim 1, wherein the medicament comprising a scorpion antivenom is administered at least twice.

18. The treatment of claim 17, wherein the administrations are at least seven days apart.

19. The treatment of claim 17, further comprising measuring progression in treatment, the measuring comprising one or more of the following parameters on the subject:
measuring blood pressure and cardiac pulse of the subject before and one hour after scorpion antivenom (SVA) treatment; physical examination one week after a first SVA treatment; and evaluating patient performance status and tumor size, CBC, CEA, liver function test, and kidney function test 10 and 24 days after the first SVA treatment, whereby continuation of treatment is determined.

20. The treatment of claim 17, further comprising measuring progression in treatment, the measuring comprising one or more of the following parameters on the subject: CEA and X-ray, at least seven days after administering the medicament.

* * * * *